(12) United States Patent
Kusleika et al.

(10) Patent No.: US 10,335,262 B2
(45) Date of Patent: Jul. 2, 2019

(54) EMBOLIC PROTECTION DEVICES HAVING SHORT LANDING ZONES

(71) Applicant: Covidien LP, Mansfield, MA (US)

(72) Inventors: Richard S. Kusleika, Eden Prairie, MN (US); Steven G. Zaver, Plymouth, MN (US); Christopher G. Quinn, Minneapolis, MN (US)

(73) Assignee: Covidien LP, Mansfield, MA (US)

( * ) Notice: Subject to any disclaimer, the term of this patent is extended or adjusted under 35 U.S.C. 154(b) by 302 days.

(21) Appl. No.: 15/399,855

(22) Filed: Jan. 6, 2017

(65) Prior Publication Data

US 2017/0181836 A1 Jun. 29, 2017

Related U.S. Application Data

(60) Division of application No. 13/400,424, filed on Feb. 20, 2012, now Pat. No. 9,572,650, which is a continuation of application No. 12/020,136, filed on Jan. 25, 2008, now abandoned.

(60) Provisional application No. 60/899,312, filed on Feb. 2, 2007.

(51) Int. Cl.
*A61F 2/01* (2006.01)
*A61B 17/12* (2006.01)

(52) U.S. Cl.
CPC .......... *A61F 2/013* (2013.01); *A61B 17/1204* (2013.01); *A61B 17/12031* (2013.01); *A61F 2002/018* (2013.01); *A61F 2230/0008* (2013.01); *A61F 2230/008* (2013.01);
(Continued)

(58) Field of Classification Search
CPC ........ A61F 2002/018; A61F 2230/0008; A61F 2230/0067; A61F 2230/008; A61F 2/013
USPC ...... 606/200, 194, 198, 159; 623/1.11, 1.12, 623/903
See application file for complete search history.

(56) References Cited

U.S. PATENT DOCUMENTS 5,911,734 A 6/1999 Tsugita et al.
5,941,896 A 8/1999 Kerr
(Continued)

FOREIGN PATENT DOCUMENTS

DE 29824846 U1 12/2002
EP 1179321 A2 2/2002
(Continued)

OTHER PUBLICATIONS

Examination Report from counterpart European Patent Application No. 08714001.8, dated Jan. 8, 2015, 4 pp.
(Continued)

*Primary Examiner* — Anh T Dang

(57) ABSTRACT

The invention provides an embolic protection device for removing emboli from a blood vessel in a patient's body. The device comprises an elongate host element, an embolic protection element having a collapsed configuration and an expanded configuration, and a flexible tether connected to a distal end of the host element and to a proximal portion of the embolic protection element. The tether allows the host element to move axially and laterally relative to the embolic protection element over a limited range of motion when the embolic protection element is in an expanded configuration. The embolic protection device has a landing zone of 4 cm or less.

27 Claims, 5 Drawing Sheets

(52) U.S. Cl.
CPC ... *A61F 2230/0067* (2013.01); *A61F 2240/00* (2013.01); *A61F 2250/0098* (2013.01)

(56) References Cited

U.S. PATENT DOCUMENTS

| | | | |
|---|---|---|---|
| 5,989,271 A * | 11/1999 | Bonnette | A61B 17/32037 604/22 |
| 6,245,012 B1 | 6/2001 | Kleshinski | |
| 6,325,815 B1 | 12/2001 | Kusleika et al. | |
| 6,773,448 B2 | 8/2004 | Kusleika et al. | |
| 6,843,798 B2 | 1/2005 | Kusleika et al. | |
| 6,932,830 B2 | 8/2005 | Ungs | |
| 7,014,647 B2 | 3/2006 | Brady et al. | |
| 7,094,249 B1 | 8/2006 | Broome et al. | |
| 7,192,434 B2 | 3/2007 | Anderson et al. | |
| 9,572,650 B2 | 2/2017 | Kusleika et al. | |
| 2002/0095171 A1 | 7/2002 | Belef | |
| 2003/0130681 A1 | 7/2003 | Ungs | |
| 2003/0130685 A1 | 7/2003 | Daniel et al. | |
| 2003/0171771 A1 | 9/2003 | Anderson et al. | |
| 2004/0093012 A1 | 5/2004 | Cully et al. | |
| 2004/0098032 A1 | 5/2004 | Papp et al. | |
| 2004/0147955 A1 | 7/2004 | Beulke et al. | |
| 2005/0228438 A1 | 10/2005 | Sachar et al. | |
| 2006/0149312 A1 | 7/2006 | Arguello et al. | |
| 2006/0229658 A1 | 10/2006 | Stivland | |
| 2006/0247675 A1 | 11/2006 | Becker et al. | |
| 2006/0287701 A1 | 12/2006 | Pal | |
| 2008/0188886 A1 | 8/2008 | Kusleika et al. | |
| 2012/0150212 A1 | 6/2012 | Kusleika et al. | |

FOREIGN PATENT DOCUMENTS

| | | |
|---|---|---|
| WO | 0204040 A2 | 1/2002 |
| WO | 03011187 A2 | 2/2003 |
| WO | 03075997 A1 | 9/2003 |
| WO | 03077799 A2 | 9/2003 |
| WO | 2004026175 A1 | 4/2004 |
| WO | 2006108186 A1 | 10/2006 |

OTHER PUBLICATIONS

International Search Report and the Written Opinion from counterpart International Application No. PCT/US2008/052039, dated May 21, 2008, 15 pp.

International Preliminary Report on Patentability from counterpart International Application No. PCT/US2008/052039, dated Aug. 4, 2009, 8 pp.

Prosecution History from U.S. Appl. No. 12/020,136, dated May 11, 2010 through Dec. 28, 2011, 144 pp.

Prosecution History from U.S. Appl. No. 13/400,424, dated Jan. 7, 2013 through Oct. 28, 2016, 262 pp.

Extended Search Report from counterpart European Application No. 18166221.4, dated Aug. 3, 2018, 5 pp.

* cited by examiner

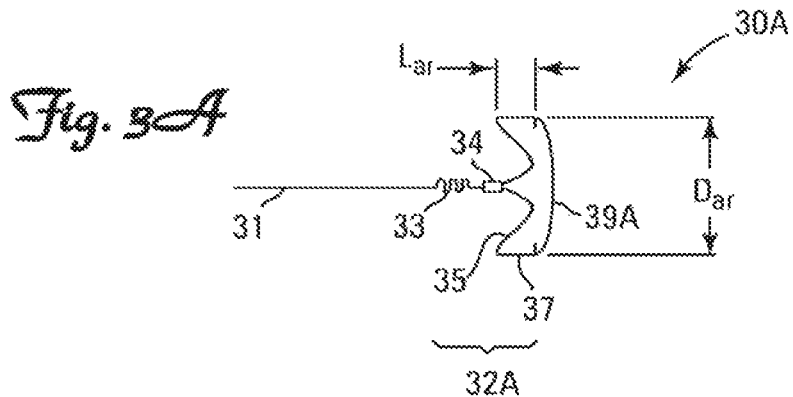
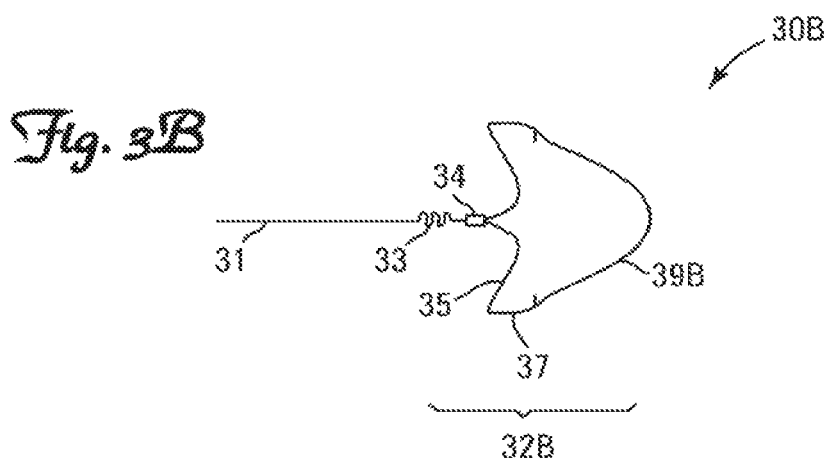
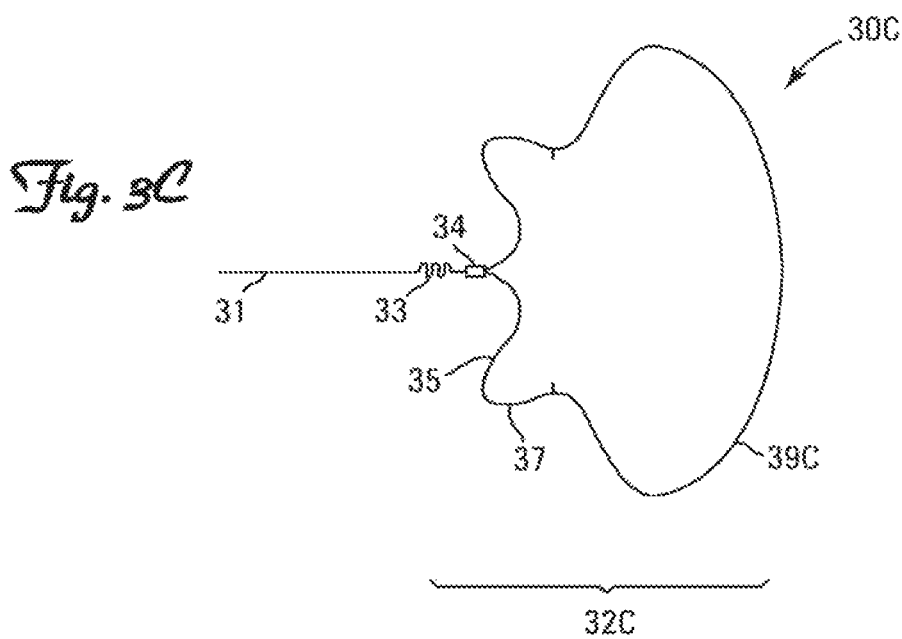

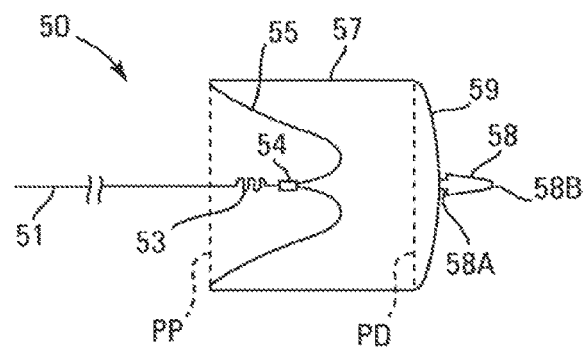
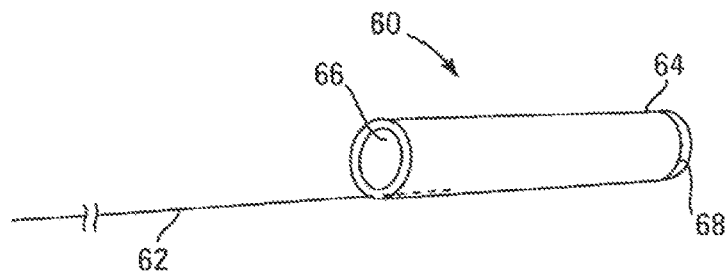
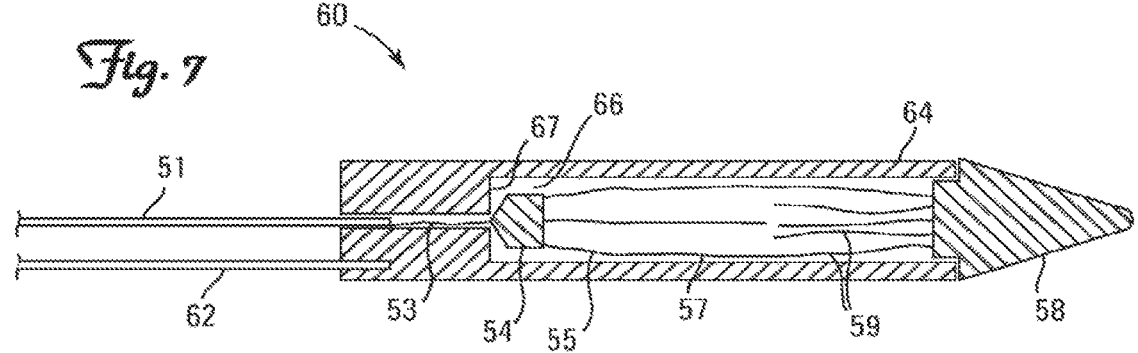

EMBOLIC PROTECTION DEVICES HAVING SHORT LANDING ZONES

This application is a divisional of U.S. patent application Ser. No. 13/400,424 filed Feb. 20, 2012, now patented as U.S. Pat. No. 9,572,650, which is a continuation of U.S. patent application Ser. No. 12/020,136, filed Jan. 25, 2008, which claims the benefit of U.S. Provisional Application No. 60/899,312, filed Feb. 2, 2007, the contents of each of which are hereby incorporated by reference herein.

FIELD OF THE INVENTION

The present invention relates to embolic protection systems, and, more particularly, to embolic protection systems for use in blood vessels.

BACKGROUND OF THE INVENTION

Vessels are commonly treated to reduce or eliminate narrowings caused by arteriosclerotic disease. Interventional treatments can include use of balloon angioplasty, stenting, thrombectomy, atherectomy, and other procedures. During treatment particulate debris can be generated at the treatment site. Infarcts, strokes, and other major or minor adverse events are caused when debris embolizes into vasculature from the treatment site.

To prevent embolization of debris, embolic protection devices have been developed. During a procedure such devices can be placed in a length of vessel, commonly referred to as a landing zone, distal or proximal to the treatment site. Embolic protection devices can remove emboli from the bloodstream by filtering debris from blood, by occluding blood flow followed by aspiration of debris, or can cause blood flow reversal to effect removal of debris. The shape, length and other characteristics of an embolic protection device are typically chosen based on the anatomical characteristics in the vicinity of the treatment site. However, some anatomies present specific challenges due to the anatomical shape or configuration.

Some anatomies have little or no room for deployment of an embolic protection device near to a treatment site. For example, lesions in the distal portion of a coronary artery bypass graft have short lengths of graft distal to the lesion, and the native vessel distal to the graft anastomotic site is often too small in diameter for satisfactory deployment of a distal embolic protection device. Further, coronary artery bypass grafts can have extensive diffuse disease and suitable landing zones of comparatively healthy conduit can very short. In yet another example, vessels that branch immediately distal to a treatment site, such as renal arteries, have very short landing zones in the short common vessel distal segment. In another example, easily damaged structures, such as the petrous segment of the internal carotid artery, can be located distal to an intended treatment site, and an embolic protection device with a long landing zone can damage these structures.

Some devices have long filtering and/or wire tip structures and these structures contribute to the overall landing zone length of the device. If the filtering portion of the device is reduced in length the capacity of the filter for debris capture and recovery can be reduced. Some devices have wire structures that are attached to a filtering or occlusive structure in a way that allows treatment devices, such as balloon angioplasty catheters, to deflect the embolic protection device away from the wall of the vessel, being treated, thereby allowing embolic debris to bypass the embolic protection device.

Some known embolic protection devices have landing zones ranging from 5 to 12 cm in length, and due to these long lengths these devices cannot protect a number of anatomical sites from embolic debris released by treatment devices.

What is needed are embolic protection devices having short landing zones, that are not deflected by treatment devices, and that have adequate debris capture and recovery capacity.

SUMMARY OF THE INVENTION

The invention provides an embolic protection device for removing emboli from a blood vessel in a patient's body, comprising: an elongate host element; an embolic protection element having a collapsed configuration and an expanded configuration; and a flexible tether connected to a distal end of the host element and to a proximal portion of the embolic protection element, the tether allowing the host element to move axially and laterally relative to the embolic protection element over a limited range of motion when the embolic protection element is in an expanded configuration, and the embolic protection device having a landing zone of 4 cm or less.

The invention provides a method for removing emboli from a blood vessel in a patient's body comprising providing an embolic protection device of the invention and introducing the embolic protection device into a vessel in the patient's body.

According to one aspect the present invention provides an embolic protection device having a short landing zone comprising a host wire, a tether, connecting arms, an apposition ring, and filtering mesh. These structures cooperate to form a recoverable embolic protection device that is insulated from host wire motion, has adequate debris capture capability, has good conduit wall apposition, and has a landing zone shorter than the conduit in which the device is deployed. Methods are provided whereby embolic protection devices having short landing zones are used with sheaths during interventional treatment of a patient.

It is to be understood that that both the foregoing general description and the following detailed description are exemplary and explanatory and are intended to provide further explanation of the invention as claimed.

BRIEF DESCRIPTION OF THE DRAWINGS

The above and further advantages of the invention may be better understood by referring to the following description in conjunction with the accompanying drawings.

FIGS. 3A, 3B and 3C illustrate conceptually side views of an embolic protection device having a landing zone in accordance with the present invention.

FIG. 5 illustrates conceptually a side view of an embolic protection device having a landing zone in accordance with the present invention.

FIG. 6 illustrates conceptually an isometric view of sheath used with an embolic protection device in accordance with the present invention.

FIG. 7 illustrates conceptually a partial cross sectional view of an embolic protection device and sheath assembly in accordance with the present invention.

DETAILED DESCRIPTION

Figure 1:
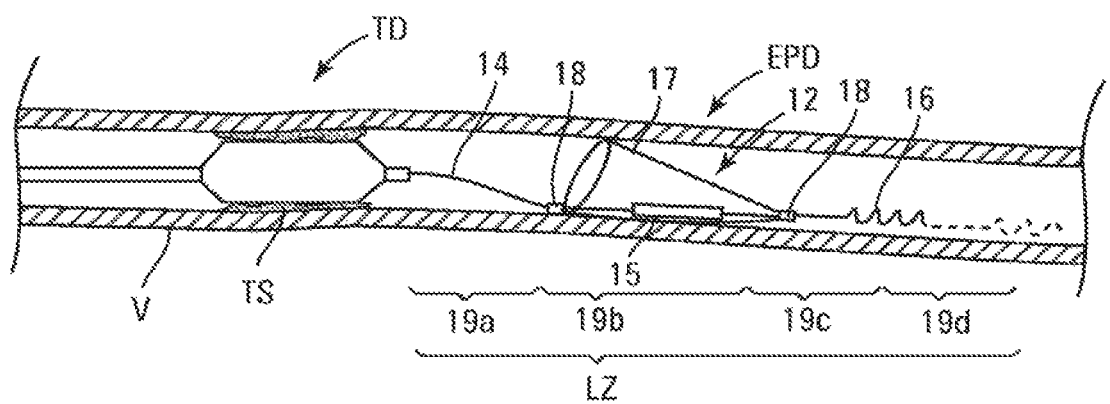
FIG. 1 illustrates conceptually a side view of a prior art embolic protection device having a landing zone.

The invention provides an embolic protection device for removing emboli from a blood vessel in a patient's body, comprising: an elongate host element; an embolic protection element having a collapsed configuration and an expanded configuration; and a flexible tether connected to a distal end of the host element and to a proximal portion of the embolic protection element, the tether allowing the host element to move axially and laterally relative to the embolic protection element over a limited range of motion when the embolic protection element is in an expanded configuration, and the embolic protection device having a landing zone of 4 cm or less. In embodiments of the invention, the device has a landing zone of 3 cm or less, 2 cm or less, or 1 cm or less.

In one embodiment, the embolic protection element comprises one or more connecting arms, an apposition ring, and a mesh, the one or more connecting arms each being connected to the tether and the apposition ring, and the apposition ring being connected to the mesh. In an embodiment, the one or more connecting arms are connected to the tether by a marker. In an embodiment, the mesh comprises a tip. In one embodiment the tip is centered in the mesh when the embolic protection element is in an expanded configuration and in another embodiment the tip has a conical shape.

In embodiments of the invention, the embolic protection element expands to establish at least line contact with substantially all of a lumenal cross section of a 2 mm to 4 mm vessel, a 3 to 6 mm vessel, a 4 to 7 mm vessel, a 2 to 7 mm vessel, a 5 to 12 mm vessel, a 10 to 20 mm vessel, or a 20 to 35 mm vessel.

In one embodiment, the mesh is a filtering mesh and has a shape in the expanded configuration which defines an interior portion having a proximal facing opening. In an embodiment, in the expanded configuration of the embolic protection element, the apposition ring has a maximum diameter and the maximum diameter of the mesh is greater than the maximum diameter of the apposition ring. In one embodiment, the maximum diameter of the mesh is at least 10 percent greater than the maximum diameter of the apposition ring. In an embodiment, the connecting arms are disposed only within the interior portion of the filtering mesh and a lumen of the apposition ring when the embolic protection element is in the expanded configuration.

In embodiments of the invention the apposition ring comprises one or more serpentine rows, one or more interconnected cells, or a slotted tube. In embodiments of the invention, the mesh is a filtering mesh that comprises a polymer film having holes or the mesh is a filtering mesh that comprises braided metal strands. In an embodiment, the maximum apposition ring diameter is from 1 mm to 35 mm. In one embodiment, the mesh comprises radiopaque materials. In one embodiment, the mesh is a filtering mesh and the mesh is held taut when the embolic protection element is in the expanded configuration.

In embodiments of the invention the embolic protection device comprises a filtering mesh or is fully occlusive. In embodiments of the invention the embolic protection element is self-expanding or self-contracting. In embodiments of the invention the embolic protection element is actively expanded or actively contracted. In one embodiment, the embolic protection device comprises radiopaque portions. In another embodiment, the elongate host element has a length of from 60 cm to 320 cm. In an embodiment, the distal end of the host element can be moved axially 5 cm without disturbing the position of the embolic protection element when the embolic protection element is in the expanded configuration.

In an embodiment, the device further comprises a sheath disposed over a portion of the embolic protection element. In embodiments of the invention the tether is in the form of a string or coil. In an embodiment, the elongate host element is a wire.

The invention provides a method for removing emboli from a blood vessel in a patient's body comprising providing an embolic protection device of the invention and introducing the embolic protection device into a vessel in the patient's body. In an embodiment, the method further comprises advancing the embolic protection device through the vessel until the embolic protection element is positioned at a desired location distal to a treatment site and deploying the embolic protection element to its expanded configuration. In an embodiment, the device further comprises a sheath disposed over a portion of the embolic protection element. In one embodiment, the method further comprises advancing the embolic protection device through the vessel until the embolic protection element is positioned at a desired location distal to a treatment site and deploying the embolic protection element to its expanded configuration by removing the sheath from the embolic protection element. In an embodiment, a guide catheter or guide lumen is advanced into the vessel in the patient's body to assist in introducing the embolic protection device. In one embodiment, a recovery catheter is used to recover the embolic protection device. In another embodiment, the method further comprises advancing a medical device for diagnosis or treatment over the elongate host element.

In the description below the invention is described using, as examples, filter mesh comprised of perforated polymer films. It is to be understood that the invention is not limited to the examples below. For example, the mesh of the invention can comprise strands that are woven, non-woven, braided, or knitted to form the mesh. The mesh can have uniform strand spacing so as to define a structure with relatively uniformly sized openings between strands or can have variable strand spacing so as to define a structure with varied size openings between strands. The mesh can be coated with an elastic polymer film in whole or in part, or with another material, so as to reduce in size or eliminate the openings between strands. The coated or uncoated mesh may be partially or totally occlusive to flow of fluid or particles therethrough. In some embodiments the metal strands may be superelastic alloys comprised of radiopaque alloy constituents. In some embodiments one or more metal strands comprise nickel-titanium-platinum or nickel-titanium-tantalum alloy. In addition, some or all of the strands may comprise materials other than metal including but not limited to engineering polymers such as PEEK (polyetheretherketone), liquid crystal polyamide, or polyester; ceramics; glass-ceramics; metallic glasses; or other materials known in the art. In some embodiments the aforementioned materials can comprise radiopaque filler materials. It is further understood that the cross section of some or all of the strands can be round, ovoid, square, rectangular, triangular, irregular, symmetrical, non-symmetrical, or other shapes.

In another aspect of the invention, the mesh can comprise a polymer film with holes produced by laser drilling, casting followed by dissolution of substances such as salts (leaving holes where the salt was dissolved), casting or forming into molds, or other methods as are known in the art. The mesh may be supported in whole or in part by struts comprising metal, polymer, ceramic, metallic glass, or other materials. The struts may be aligned along the longitudinal axis of the embolic protective device, transverse to the longitudinal axis of the device, a combination of the two, or other orientations.

In the description below the invention is further described using as examples an embolic protective device having a generally cylindrical shape and a proximal facing opening. It is to be understood that the invention is not limited to the examples below. For example, the embolic protective device of the invention can have a variety of other shapes such as generally conical, cup-shaped, generally planar, or any other shape and may have a distally facing opening, proximal and distal openings, an opening off axis from the central longitudinal axis of the device, a sidewall opening, and no opening at all. The embolic protective device may be self-expanding, that is, have a tendency to radially or longitudinally expand, or both, when unconstrained; may be self-contracting, be partially self-expanding and partially self-contracting, or may have no tendency to either expand or contract when not constrained. The embolic protective device may also be actively actuated radially or longitudinally or both by attaching a proximal end and a distal end of the device to telescoping structures, by using an inflatable structure such as a balloon to expand and contract the device, or by using other methods, as is known in the art.

Also in the description below, the invention is described as comprising radiopaque elements applied to an embolic protective device generally in the region of a proximal facing opening. It is to be understood that the invention is not limited to the examples below. For example, the radiopaque elements can be applied to an embolic protective device at other locations or regions of interest such as on the body of the device, at a midpoint of the device, at the distal end of the device, on ancillary structures other than the mesh of the device, and at other locations on the device.

It is understood that the radiopaque elements discussed below can comprise a range of radiopaque materials known in the art. Materials such as platinum, rhenium, iridium, tungsten, gold, lead, barium sulphate, bismuth oxychloride, bismuth subcarbonate, lead oxide, iodine-containing compounds, barium-containing compounds, ceramics, metallic glasses, and others may be used. Various physical forms comprising radiopaque materials can be prepared and applied to embolic protective devices, such as monofilament wires, composite wires, stranded wires, cables, sheet, strip, mesh, sponge, sintered powders, powders or fibers embedded into matrices such as polymer matrices, tubes, and other forms.

FIG. 1 illustrates prior art embolic protection device EPD having landing zone LZ. Embolic protection device EPD comprises filter 12 mounted on host wire 14 having stop 15 and floppy tip 16. Filter 12 comprises mesh 17 attached to sliders 18. For clarity, mesh 17 is shown in outline form and individual pores in the mesh are not illustrated. Further descriptions of a filter similar to that illustrated in FIG. 1 are disclosed in U.S. Pat. No. 6,325,815 B1 to Kusleika et. al., entitled "Temporary Vascular Filter" and in U.S. Pat. No. 6,843,798 B2 to Kusleika et al., entitled "Slideable Vascular Filter", the contents of both of which are incorporated herein by reference. Treatment device TD has been advanced over host wire 14 and deployed at treatment site TS in vessel V. Landing zone LZ is comprised of distance 19*a* between treatment device TD and filter 12, length 19*b* of deployed filter 12, length 19*c* of portion of host wire 14 and floppy tip 16 distal to filter 12, and distance 19*d* that stop 15 can move between sliders 18 when filter 12 is deployed in vessel V.

Distance 19*a* is provided to assure that interactions between treatment device TD and filter 12 that tend to decrease filter mesh 17 apposition against lumenal surface of vessel V are minimized. Distance 19*a* is commonly specified by device manufacturers and known examples range from 1.5 cm to 3.0 cm. Distances 19*b* and 19*c* are consequences of the embolic protection device EPD design. Distance 19*b* is known to range from 1.0 cm to 3.0 cm and distance 19*c* is known to range from 2.0 cm to 5.0 cm. Distance 19*d* is a consequence of providing a limited amount of axial movement of host wire 14 relative to filter mesh 17 so that catheters can be exchanged over host wire 14 without causing excessive motion of filter 12 in vessel V. Distance 19*d* is known to range from 0.0 cm to 1.5 cm. Landing zone LZ for various known devices will therefore vary from approximately 4.5 cm to approximately 12.5 cm.

Figure 2A:
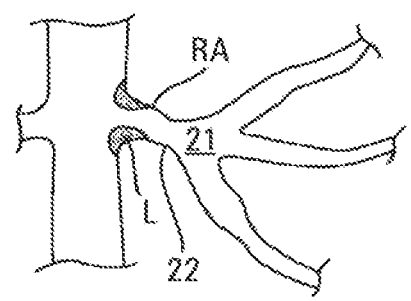
FIGS. 2A and 2B illustrate conceptually section views of anatomies having treatment locations suitable for use of embolic protection devices with short landing zones.
Figure 2B:
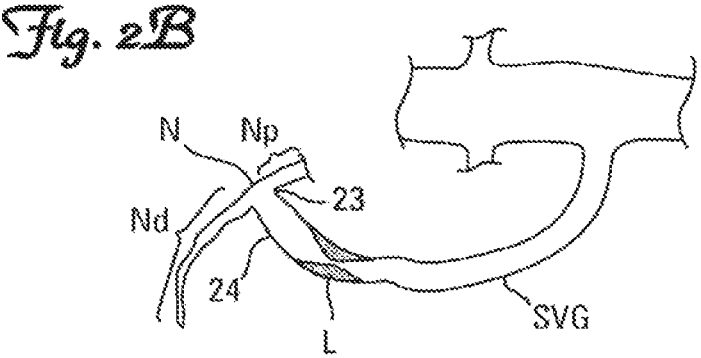

FIGS. 2A and 2B illustrate anatomies having treatment locations that could benefit from use of embolic protection devices having short landing zones. FIG. 2A represents renal artery RA having lesion L. Renal artery RA trifurcates at location 21. In a typical patient, renal artery length varies from 2 to 5 cm, lesion L length varies from 1 to 2 cm, and lesion L is located in the vicinity of the renal artery ostium. A distal embolic protection device is desirably placed at location 22 in the relatively undiseased portion of the renal artery, distal to the lesion and proximal to trifurcation location 21. The landing zone length of known embolic protection devices is too long for satisfactory deployment of the known devices at location 22.

FIG. 2B represents saphenous vein graft SVG having lesion L. Saphenous vein graft SVG is joined to native coronary artery N at anastomotic site 23. Native coronary artery N is comprised of proximal portion Np and distal portion Nd. In a typical patient, saphenous vein graft length varies from 10 to 20 cm and a distal embolic protection device is desirable placed distal to lesion L at location 24. If a distal embolic protection device is placed in coronary artery proximal portion Np then distal portion Nd of coronary artery N will be unprotected. If a distal embolic protection device is placed in coronary artery distal portion Nd then proximal portion Np of coronary artery N will be unprotected. The landing zone length of known embolic protection devices is too long for satisfactory deployment of the known devices at location 24 when the lesion is in a distal portion of saphenous vein graft SVG.

FIGS. 3A, 3B and 3C illustrate embolic protection devices having landing zones in accordance with the present invention. Embolic protection devices 30A, 30B, and 30C comprise host wire 31, tether 33, marker 34, arms 35, apposition ring 37, and mesh 39A, 39B, and 39C respectively. Host wire 31 may be comprised of any material that will provide adequate support and lubricity for interventional devices to be advanced thereover, typically a metal such as stainless steel, nitinol, metallic glass, or other materials, with or without a lubricious coating. In some embodiments host wire 31 comprises a radiopaque marker (not shown) in the distal region of the host wire. In some examples host wire 31 diameters range from 0.009" (0.023 cm) to 0.038" (0.097 cm), and host wire 31 lengths range from 60 cm to 320 cm.

Tether 33 is flexible and is dimensioned such that host wire 31 can move axially or laterally relative to marker 34 without disturbing the position of the marker. In one embodiment host wire 31 in vicinity of tether 33 can be in contact with the lumenal wall of the vessel without disturbing the position of the marker. In one embodiment host wire 31 can be displaced axially relative to marker 34 by as much as 5 cm without disturbing the position of the marker. One end of tether 33 is attached to host wire 31 and the other end of the tether is attached to marker 34. Tether 33 is attached to host wire 31 by bonding, welding, soldering, brazing, crimping, swaging, or other means known to those of skill in the art. In one embodiment a socket is machined into the end of host wire 31 by electrical discharge machining (EDM), tether 33 is inserted into the socket, and the end of the host wire is swaged around tether 33. Tether 33 may be comprised of any material that will allow interventional devices to be advanced over the tether, typically a metal such as stainless steel, nitinol, metallic glass; or suture, braided polyester, KEVLAR® fiber, or other materials, with or without a lubricious coating. In some embodiments tether 33 is comprised of stranded wire, and in other embodiments the tether is comprised of cable. In some embodiments the diameter of tether 33 is approximately equal to the diameter of host wire 31. Tether 33 can have any form such as a string, a coil, etc.

Marker 34 is attached to tether 33 and arms 35 and may comprise metals, adhesives, polymers, weldments, brazed assemblies, or other structures. In some embodiments marker 34 comprises radiopaque materials such as gold, platinum and its alloys, or other materials as are known in the art. In other embodiments marker 34 comprises non-radiopaque materials such as stainless steel. Marker 34 may comprise a tube of material and may function as a connector for tether 33 and arms 35. In one embodiment tether 33 and arms 35 are inserted into tubular marker 34 and the tubular marker is swaged around tether 33 and arms 35 to connect them. Marker 34 may be comprised of flexibility enhancing structure (not shown) such as slots, slits, holes, reduced thickness regions, annealed regions, or other structure.

One or more arms 35 are attached to marker 34 and to apposition ring 37. Arms 35 may be attached to apposition ring 37 by bonding, welding, soldering, brazing, crimping, swaging, or other means known to those of skill in the art. Arms 35 may be integrally formed with apposition ring 37 by processes such as laser cutting, machining, stamping, forming, or etching of sheet materials or of tubing, may be electroformed, vapor deposited, sputter formed, or may be otherwise formed by processes known to those of skill in the art. Arms 35 may comprise flexible metals or polymers such as nitinol, stainless steel, polyester, nylon, tantalum, platinum, gold, or other materials. In some embodiments arms 35 have a zig-zag shape along their length. In other embodiments arms 35 have a serpentine shape along their length. In one embodiment arms 35 and marker 34 lie within a volume defined by a plane PP bounded by the proximal most portions of apposition ring and a plane PD bounded by the distal most portions of apposition ring (see FIG. 5). When embolic protection device 30A, 30B, or 30C is pulled into a tube by first loading the proximal end of the host wire into the distal end of the tube, and then pulling on host wire 31 to draw arms 35 into the tube, arms 35 will substantially straighten, and continued pulling on host wire will draw the apposition ring into the tube (see FIG. 7).

Apposition ring 37 is attached to one or more arms 35 and mesh 39A, 39B, or 39C. Apposition ring 37 may be formed by processes such as laser cutting, machining, stamping, forming, or etching of sheet materials or of tubing, may be electroformed, vapor deposited, sputter formed, or may be otherwise formed by processes known to those of skill in the art. Apposition ring 37 may comprise flexible metals or polymers such as nitinol, stainless steel, polyester, nylon, tantalum, platinum, gold, or other materials. In some embodiments apposition ring 37 comprises a slotted tube. In other embodiments apposition ring 37 comprises a cellular pattern cut from a thin sheet of metal. In one embodiment arms and apposition ring are integrally formed by laser cutting a tube of superelastic nitinol into the desired pattern and heat setting the cut tube into a preprogrammed self-expanding shape. When apposition ring 37 is expanded in a vessel, the apposition ring maintains close contact with the lumenal wall of the vessel so that emboli generated upstream of the apposed ring 37 cannot pass between apposition ring 37 and the wall of the vessel. When embolic protection device 30A, 30B, or 30C is pulled into a tube by first loading the proximal end of the host wire into the distal end of the tube, and then pulling on host wire 31 to draw arms 35 and apposition ring 37 into the tube, apposition ring 37 will collapse into the tube and continued pulling on host wire will draw mesh 39A, 39B, and 39C into the tube (see FIG. 7). Apposition ring thicknesses between 0.001" (0.0025 cm) and 0.020" (0.051 cm) are contemplated.

Figure 4A:
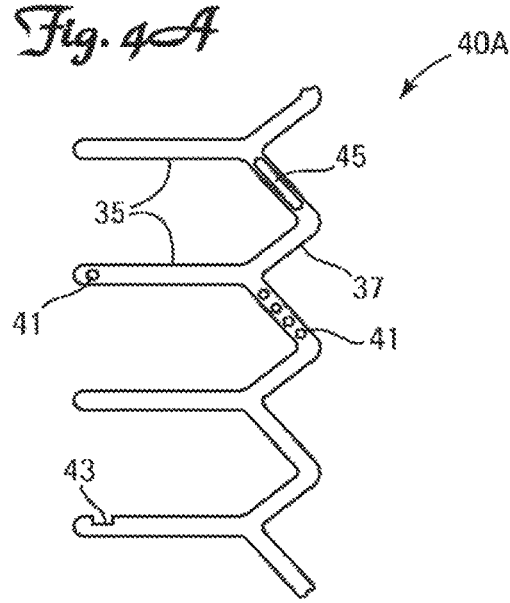
FIGS. 4A, 4B and 4C illustrate conceptually a component of an embolic protection device having a landing zone in accordance with the present invention.
Figure 4B:
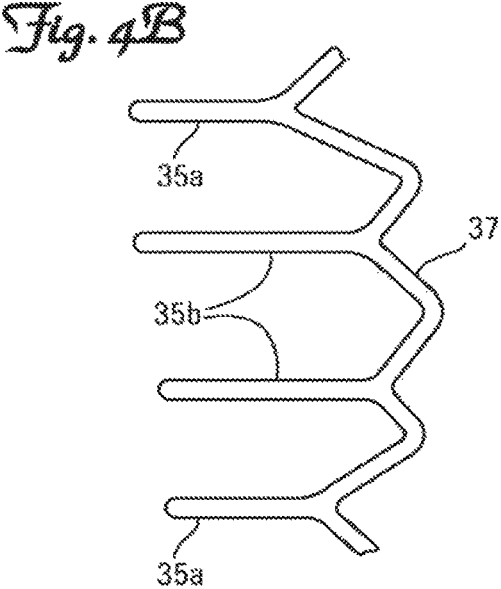
Figure 4C:
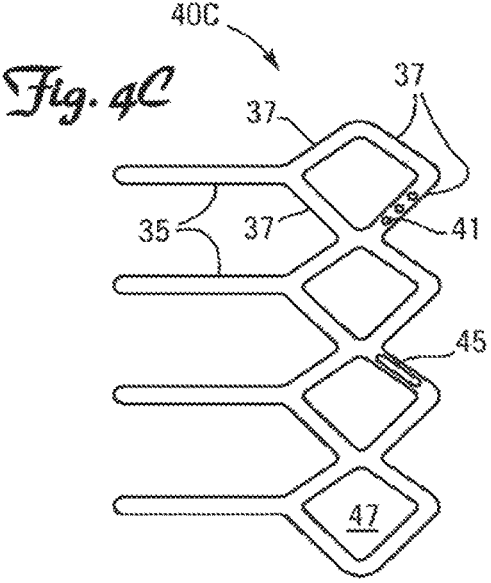

FIGS. 4A, 4B and 4C illustrate integrally formed apposition ring and arm structures 40A, 40B, and 40C, laser cut from tubes of superelastic nitinol into the desired pattern. For convenience of illustration the laser cut tubes are shown cut lengthwise, unrolled and laid flat. Apposition rings 37 may comprise serpentine rows, may comprise interconnected cells 47, or may have other structures. FIG. 4A illustrates one example 40A of an apposition ring serpentine row connected to arms 35 having equal lengths. FIG. 4B illustrates another example 40B of an apposition ring serpentine row connected to arms $35a$, $35b$ having different lengths. Apposition ring and arm structure 40B has a lower compressed profile than apposition ring and arm structure 40A due to arms $35a$, $35b$ having different lengths. Arms $35a$, $35b$ may comprise one or more notches 43 to improve mechanical interlock of attachment between arms and marker 34. Although a notch 43 is illustrated in FIG. 4A it is understood that cutouts, surface roughness, projections, protuberances, or other structures can also improve mechanical interlock of attachment between arms and marker 34. FIG. 4C illustrates an example 40C of an apposition ring 37 having one row of interconnected cell 47 structure connected to arms 35. It is understood that apposition ring 37 may comprise two rows, three rows, or four or more rows of interconnected cell structure connected to arms 35.

In one embodiment maximum apposition ring diameter $D_{ar}$ (see FIG. 3A) is about 5% larger than the diameter of the largest vessel or conduit in which embolic protection device 30A, 30B, or 30C will be used. In other embodiments, maximum apposition ring diameters D are about 10% larger, about 15% larger, or about 20% larger than the diameter of the largest vessel or conduit in which embolic protection device 30A, 30B, or 30C will be used. It is contemplated that maximum apposition ring diameter D can be of any percentage from about 2% larger to about 25% larger than the diameter of the largest vessel or conduit in which the embolic protection device 30A, 30B, or 30C will be used. Maximum apposition ring diameters can range from 1 mm to 35 mm. In embodiments of the invention, the maximum apposition ring diameter can be 4 mm, 6 mm, 7 mm, 12 mm, 20 mm, or 35 mm. In one embodiment maximum apposition ring diameters are designed for vessels ranging from 2 mm to 4 mm. In another embodiment maximum apposition ring diameters are designed for vessels ranging from 3 mm to 6 mm. In another embodiment maximum apposition ring diameters are designed for vessels ranging from 4 mm to 7 mm. In another embodiment maximum apposition ring diameters are designed for vessels ranging from 2 mm to 7 mm. In another embodiment maximum apposition ring diameters are designed for vessels ranging from 5 mm to 12 mm. In another embodiment maximum apposition ring diameters are designed for vessels ranging from 10 mm to 20 mm. In another embodiment maximum apposition ring diameters are designed for vessels ranging from 20 mm to 35 mm. Contemplated apportion ring lengths $L_{ar}$ (see FIG. 3A) range from 10% to 250% of apposition ring diameter. In one embodiment apposition ring length is 25% of maximum apposition ring diameter. In another embodiment apposition ring length is 50% of maximum apposition ring diameter. In another embodiment apposition ring length is 100% of maximum apposition ring diameter. In another embodiment apposition ring length is 150% of maximum apposition ring diameter. In another embodiment apposition ring length is 200% of maximum apposition ring diameter.

Mesh 39A, 39B, or 39C is attached to apposition ring 37 by bonding, fusing, welding, riveting, thermoforming, covalently bonding, or other processes as are known to those of skill in the art. Apposition ring 37 may be provided with one or more holes 41, slots 45, surface roughness, chemical primer layer, chemical functional group, or other means to improve strength of attachment between apposition ring and mesh (see FIGS. 4A to 4C). In one embodiment apposition ring is provided with holes 41 over substantially all of the length to which it is bonded to mesh. In another embodiment mesh is fused to apposition ring using a thermoplastic polymer adhesive. In one embodiment apposition ring 37 is provided with holes 41 in the proximal region of the ring and the holes are filled with radiopaque materials. In another embodiment one or more arms 35 are provided with holes 41 in the region near apposition ring 37 and the holes are filled with radiopaque materials.

In some embodiments mesh 39A, 39B, or 39C has a tip attached thereto. FIG. 5 illustrates embolic protection device 50 comprising host wire 51, tether 53, marker 54, arms 55, apposition ring 57, tip 58, and mesh 59. Host wire 51, tether 53, marker 54, arms 55, apposition ring 57, and mesh 59 have substantially the same materials of construction and function as host wire 31, tether 33, marker 34, arms 35, apposition ring 37, and mesh 39 respectively (described earlier). Tip 58 is attached to mesh 59 by bonding, fusing, welding, riveting, thermoforming, or other processes as are known to those of skill in the art. In one embodiment the tip is fused to the mesh using a thermoplastic polymer adhesive. Tip 58 comprises soft material such as polyether block amide (for example PEBAX® polymer), rubber, silicone, thermoplastic elastomer, styrene-ethylene-butylene-styrene block copolymer such as C-FLEX® polymer, or other materials and may also comprise radiopaque materials including barium sulphate, bismuth oxychloride, bismuth subcarbonate, tungsten powder, platinum, or gold. Tip 58 has recess 58A sized to fit into a sheath such as sheath 60 illustrated in FIG. 6 and discussed in further detail in connection with FIG. 7. Largest diameter of tip 58 is sized to be substantially similar to the outside diameter of a sheath such as sheath 60. Tip 58 tapers to a rounded point at tip distal end 58B.

Mesh 39A, 39B, or 39C comprises a thin sheet of material having openings therethrough. For clarity in the Figures, only the mesh perimeter is shown, and the mesh perforations are not shown. Mesh can be made in a number of ways and be constructed from a number of materials as described earlier. Mesh thicknesses from 0.0002" (0.0005 cm) to 0.005" (0.013 cm) are contemplated. Mesh pore size is chosen such that substantially all emboli of a size that could cause harm to downstream tissues are prevented from traversing mesh. Mesh pore sizes from 50 microns to 500 microns are contemplated. In some embodiments the mesh must be occlusive so that harm to downstream tissues is prevented. In one embodiment the mesh is comprised of a 0.001" (0.0025 cm) thick biaxially oriented non-self-expanding polymer sheet having 100 micron diameter round holes laser drilled therethrough. In some embodiments the mesh comprises radiopaque materials. The mesh can be attached to apposition ring 37 with different amounts of excess mesh area. In FIG. 3A, mesh 39A is dimensioned such that when apposition ring 37 is expanded so maximum diameter mesh 39A is held taut. In FIG. 3B, mesh 39B is dimensioned such that when apposition ring 37 is expanded to maximum diameter mesh 39B forms a conical chamber. In FIG. 3C, mesh 39C is dimensioned such that when apposition ring 37 is expanded to maximum diameter mesh 39C has a diameter larger than that of the apposition ring. It is appreciated that embolic protection device 30B can contain larger volume of captured emboli than embolic protection device 30A, and that embolic protection device 30C can contain a larger volume of captured emboli than embolic protection device 30B. It is understood that those of skill in the art will vary the excess area of mesh attached to opposition ring 37 depending on the anatomical requirements and embolic load expected for a given treatment site.

Embolic protection devices 30A, 30B, and 30C have landing zones 32A, 32B, and 32C respectively. Landing zones 32A, 32B, and 32C are shorter than the landing zones of known devices in part because (1) tether 33, in a very space efficient manner, minimizes interactions between the treatment device and the embolic protection devices that tend to decrease mesh apposition against the lumenal surface of vessel, and (2) because the tip of the treatment device can be placed within the volume defined by apposition ring 37 due to flexibility of tether 33, and (3) because embolic protection device length can be short in part due to device design in which arms 35 are positioned within the volume defined by apposition ring 37, and (4) because the mesh is thin and flexible enough to be deflected away from anatomies, and (5) because embolic protection devices 30A, 30B, and 30C do not have guidewire tips. Embolic protection device landing zones 32A, 32B, and 32C ranging in length from 0.5 cm to 5 cm are contemplated. In one embodiment the landing zone is about 1 cm long. In another embodiment the lauding zone is about 2 cm long. In another embodiment the landing zone is about 3 cm long. In another embodiment the landing zone is about 4 cm long. In yet another embodiment landing zones 32A, 32B, and 32C ranging in length from 25% to 250% of vessel diameter at the embolic protection device deployment site are contemplated. In one embodiment the landing zone length is 50% of vessel diameter. In another embodiment the landing zone length is 100% of vessel diameter. In another embodiment the landing zone length is 150% of vessel diameter. In another embodiment the landing zone length is 200% of vessel diameter.

FIG. 6 illustrates sheath 60 for use with an embolic protection device in accordance with the present invention. Sheath 60 comprises control wire 62 and tubular portion 64 having soft tip 68 and lumen 66. Control wire 62 comprises metal such as stainless steel, nitinol, metallic glass, or other materials, with or without a lubricious coating. In some examples control wire 62 diameters range from 0.009" (0.023 cm) to 0.038" (0.097 cm), and control wire 62 lengths range from 60 cm to 320 cm. Tubular portion 64 comprises nylon, polyether block amide such as PEBAX® polymer, polyester, polybulylene, terephthalate-long chain polyether glycols block copolymer such as HYTREL® polymer, polyethylene, fluoropolymer, or other materials known to those of skill in the art and may be made by processes such as extrusion. Soft tip 68 comprises soft material such as polyether block amide such as PEBAX® polymer, rubber, silicone, thermoplastic elastomer, styrene-ethylene-butylene-styrene block copolymer such as C-FLEX® polymer, or other materials and may also comprise radiopaque materials including barium sulphate, bismuth oxychloride, bismuth subcarbonate, tungsten powder, platinum, or gold. Soft tip 68 and control wire 62 are bonded to tubular portion 64 by molding, use of adhesives, solvent bonding, or other means. Tubular portion 64 has lumen 66 that slideably receives embolic protection device 30A, 30B, 30C, or 50. Lumen 66 may have shoulder 67 (see FIG. 7) to prevent passage of marker 34, 54 through the lumen proximal to the shoulder.

FIG. 7 illustrates embolic protection device 50 assembled within sheath 60. Proximal end of host wire 51 has been inserted into the distal end of tubular portion 64 and withdrawn proximally to draw tether 53, marker 54, arms 55, apposition ring 57, and mesh 59 into lumen 66. Tip 58 has been drawn into contact with the distal end of tubular portion 64 and recess 58A of tip has been drawn into lumen 66 of tubular portion 64.

An illustrative method of using an embolic protection device having a short landing zone is as follows. Percutaneous access is obtained through the skin of a patient using methods known in the art. A sheath is inserted into the patient to preserve access through the skin and optionally a guide catheter may be inserted into the patient to provide access to the region of interest. The proximal end of host wire 51 of embolic protective device 50 is inserted into the distal end of tubular portion 64 of sheath 60 and host wire 51 is drawn proximally until the marker, arms, apposition ring, mesh, and recess of the tip are contained within the tabular portion of sheath 60. Embolic protection device 50/sheath 60 assembly is advanced through the sheath and guide catheter (if used) and across the region of interest, typically a stenosis in an artery. Fluoroscopy is used by the operator to visualize marker 54 and tip 58 and to ascertain that the embolic protection device is positioned appropriately in relation to the region of interest, for example, such that the proximal opening of the apposition ring is sufficiently distal to a stenosis in an artery. Due to the short landing zone of device 50 it can be positioned, for example, in the non-diseased segment of a renal artery 22, or in another example can be positioned distal to a distal lesion in a saphenous vein graft in the heart. Sheath 60 is then withdrawn proximally, allowing apposition ring 57 to expand into contact with inner wall of vessel and allowing arms 55 to move into volume defined by apposition ring 57. Radiopaque contrast media may be injected at this time or at any time to assist with visualization of the patient's anatomy. Sheath 60 is removed from the patient and from host wire 51.

Host wire 51 is moved axially to a position in which there is no tension on tether 53 by adjusting the distance between the marker band (not shown) on the host wire and marker 54. One or move interventional treatment or diagnostic devices are advanced over host wire 51 and used to treat or diagnose the region of interest, for example by dilating a lesion with a balloon dilatation catheter or by deploying a stent or drug eluting stent at the treatment site. Apposition of apposition ring 57 to the interior wall of the vessel is preserved during catheter exchanges because flexible tether isolates motion of the host wire from the marker during catheter exchanges. Embolic material generated during diagnosis or treatment is captured by embolic protection device 50 within the volume defined by the apposition ring. After diagnosis or treatment the interventional device(s) are removed from host wire 51.

After removing the interventional device(s) from host wire 51, sheath 60 is re-advanced over the host wire to a location immediately proximal to apposition ring 57. Host wire 51 is drawn proximally, drawing first tether 53, then marker 54, then arms 55, then apposition ring 57, and finally at least a portion of mesh 59 with emboli contained therein into the tubular portion of sheath. The embolic protection device 50/sheath 60 assembly is withdrawn through the guide catheter (if used) and sheath and out of the patient.

while this document has described an invention mainly in relation to embolic protection filtering devices having short landing zones and used in vessels, it is envisioned that the invention can be applied to other conduits in the body as well including veins, bronchi, ducts, ureters, urethra, and other lumens intended for the passage of air, fluids, or solids. The invention can be applied to other devices such as vena cava filters, intracranial filters, aneurism excluders, and other devices.

While the various embodiments of the present invention have related to embolic protection filtering devices, the scope of the present invention is not so limited. Further, while choices for materials and configurations have been described above with respect to certain embodiments, one of ordinary skill in the art will understand that the materials described and configurations are applicable across the embodiments.

The above description and the drawings are provided for the purpose of describing embodiments of the invention and are not intended to limit the scope of the invention in any way. It will be apparent to those skilled in the art that various modifications and variations can be made without departing from the spirit or scope of the invention. Thus, it is intended that the present invention cover the modifications and variations of this invention provided they come within the scope of the appended claims and their equivalents.

What is claimed is:

1. An embolic protection device comprising:
an elongate host element including a host element distal portion;
an embolic protection element being movable between a collapsed configuration and an expanded configuration, wherein the embolic protection element comprises;
at least one connecting arm having a first end and a second end,
an apposition ring connected to the second end of the at least one connecting arm, wherein when the embolic protection element is deployed in the expanded configuration, the apposition ring is configured to contact a luminal wall of a blood vessel of a patient in a manner that prevents passage of emboli between the embolic protection element and the luminal wall; and
a mesh connected to the apposition ring, wherein the mesh is dimensioned such that when the apposition ring is expanded to a maximum diameter, the mesh has a diameter at least 10 percent larger than the maximum diameter of the apposition ring; and a flexible tether including a tether proximal end fixed to the host element distal portion and a tether distal end fixed to a proximal end of the embolic protection element, wherein the embolic protection element is connected to the elongate host element through the flexible tether so that the embolic protection device does not include a tip of a guidewire extending through the embolic protection element or distal to the embolic protection element, and wherein the flexible tether is configured to allow the elongate host element to move axially and laterally relative to the embolic protection element over a limited range of motion when the embolic protection element is deployed in the expanded configuration within the blood vessel.

2. The device of claim 1, wherein the embolic protection device defines a landing zone extending from the tether proximal end to a distal end of the embolic protection element wherein the landing zone does not exceed 4 centimeters (cm) when the embolic protection element is deployed within the blood vessel and the flexible tether is fully extended.

3. The device of claim 1, wherein the mesh is a filtering mesh, and wherein a lumen of the apposition ring and the mesh define a shape in the expanded configuration which defines an interior portion having a proximal facing opening.

4. The device of claim 3, wherein the at least one connecting arm is disposed only within the interior portion when the embolic protection element is in the expanded configuration.

5. The device of claim 1, wherein the mesh comprises a filtering mesh that comprises a polymer film having holes.

6. The device of claim 1, wherein the mesh comprises a filtering mesh that comprises braided metal strands.

7. The device of claim 1, wherein the apposition ring comprises a slotted tube.

8. The device of claim 1, wherein the embolic protection element is fully occlusive.

9. The device of claim 1, wherein the embolic protection element is self-expanding.

10. The device of claim 1, wherein the embolic protection element is self-contracting.

11. The device of claim 1, wherein the embolic protection element is configured to be actively expanded.

12. The device of claim 1, wherein the embolic protection element is configured to be actively contracted.

13. The device of claim 1, wherein the embolic protection device comprises radiopaque portions.

14. The device of claim 1, wherein the flexible tether is configured to allow the host element distal portion to move axially a length of the flexible tether without disturbing a position of the embolic protection element when the embolic protection element is deployed in the expanded configuration in the blood vessel.

15. The device of claim 1, wherein the maximum diameter of the apposition ring is 1 mm to 35 mm.

16. The device of claim 1, wherein the flexible tether is in the form of a coil.

17. The device of claim 1, wherein the elongate host element is a wire.

18. The device of claim 1, wherein the distal end of the embolic protection element defines a distalmost end of the embolic protection device.

19. The device of claim 1, wherein apposition ring defines a ring length, wherein the ring length is measured parallel to a central axis of the apposition ring, and wherein the ring length is 10% to 250% of the maximum diameter of the apposition ring.

20. The device of claim 1, wherein the embolic protection element further comprises:
a marker that fixes the tether distal end to the first end of the one or more connecting arms.

21. The device of claim 1, wherein the embolic protection element further comprises a soft tip attached to the mesh.

22. The device of claim 21, wherein the soft tip comprises at least one soft material selected from the group consisting of polyether block amide, rubber, silicone, thermoplastic elastomer, and styrene-ethylene-butylene-styrene block copolymer.

23. The device of claim 21, wherein the soft tip comprises a radiopaque material.

24. The device of claim 21, wherein the soft tip is fixed to a center of the mesh.

25. The device of claim 1, wherein, when the apposition ring is expanded to the maximum diameter, a portion of the mesh that defines the diameter that is at least 10 percent larger than the maximum diameter of the apposition ring is distal to the apposition ring.

26. A method of forming an embolic protection device, the method comprising:
forming an embolic protection element being movable between a collapsed configuration and an expanded configuration, the embolic protection element comprising;
at least one connecting arm having a first end and a second end,
an apposition ring connected to the second end of the at least one connecting arm, wherein when the embolic protection element is deployed in the expanded configuration, the apposition ring is configured to contact a luminal wall of a blood vessel of a patient in a manner that prevents passage of emboli between the embolic protection element and the luminal wall; and
a mesh connected to the apposition ring, wherein the mesh is dimensioned such that when the apposition ring is expanded to a maximum diameter, the mesh has a diameter at least 10 percent larger than the maximum diameter of the apposition ring;
fixing a distal end of a flexible tether to a proximal end of the embolic protection element; and
fixing a proximal end of the flexible tether to a distal portion of a elongate host element so that the embolic protection element is connected to the elongate host element through the flexible tether and the embolic protection device does not include a tip of a guidewire extending through the embolic protection element or distal to the embolic protection element, wherein the flexible tether is configured to allow the elongate host element to move axially and laterally relative to the embolic protection element over a limited range of motion when the embolic protection element is deployed in the expanded configuration within the blood vessel.

27. A method of removing emboli from a blood vessel in a patient comprising:
introducing an embolic protection device into the blood vessel in the patient, the embolic protection device comprising:
an elongate host element including a host element distal portion;
an embolic protection element being movable between a collapsed configuration and an expanded configuration, wherein the embolic protection element comprises;

at least one connecting arm having a first end and a second end, an apposition ring connected to the second end of the at least one connecting arm, wherein when the embolic protection element is deployed in the expanded configuration, the apposition ring is configured to contact a luminal wall of the blood vessel of the patient in a manner that prevents passage of emboli between the embolic protection element and the luminal wall; and a mesh connected to the apposition ring, wherein the mesh is dimensioned such that when the apposition ring is expanded to a maximum diameter, the mesh has a diameter at least 10 percent larger than the maximum diameter of the apposition ring; and a flexible tether including a tether proximal end fixed to the host element distal portion and a tether distal end fixed to a proximal end of the embolic protection element, wherein the embolic protection element is connected to the elongate host element through the flexible tether so that the embolic protection device does not include a tip of a guidewire extending through the embolic protection element or distal to the embolic protection element, and wherein the flexible tether is configured to allow the elongate host element to move axially and laterally relative to the embolic protection element over a limited range of motion when the embolic protection element is deployed in the expanded configuration within the blood vessel.

* * * * *